(12) United States Patent
Aman et al.

(10) Patent No.: US 10,952,804 B1
(45) Date of Patent: Mar. 23, 2021

(54) LIMITED USE TOOL DISPOSABLE ENCLOSURE

(71) Applicant: Insurgical Inc., Austin, TX (US)

(72) Inventors: Peter M Aman, Austin, TX (US); Frederick N Matthews, Key Largo, FL (US); Matthew Jones, Arlington, TX (US); Richard Acevedo, Austin, TX (US); Daniel Tagtow, Pine, CO (US); Roy Melling, Borrego Springs, CA (US)

(73) Assignee: Isurgical, Inc., Austin, TX (US)

( * ) Notice: Subject to any disclaimer, the term of this patent is extended or adjusted under 35 U.S.C. 154(b) by 104 days.

(21) Appl. No.: 15/965,887

(22) Filed: Apr. 28, 2018

Related U.S. Application Data

(63) Continuation of application No. 14/551,080, filed on Nov. 24, 2014, now abandoned.
(Continued)

(51) Int. Cl.
*A61B 17/14* (2006.01)
*A61B 17/16* (2006.01)
(Continued)

(52) U.S. Cl.
CPC .......... *A61B 46/10* (2016.02); *A61B 17/1622* (2013.01); *A61B 50/30* (2016.02);
(Continued)

(58) Field of Classification Search
CPC ......... A61B 46/10; A61B 50/30; A61B 50/33; A61B 17/1622; A61B 2050/0065; A61B 2050/3008; A61B 2017/0023; B25F 5/02
See application file for complete search history.

(56) References Cited

U.S. PATENT DOCUMENTS 1,497,561 A * 6/1924 Gruss .................... A61C 1/16
433/116
1,691,823 A * 11/1928 Ogilvie ................ A61C 1/16
433/116
(Continued)

FOREIGN PATENT DOCUMENTS

CN 2294028 Y 10/1998
CN 2820102 Y 9/2006
(Continued)

OTHER PUBLICATIONS

Ouyang; "Drilling to the Problem: Low-Cost Sterile Drill Covers for Surgery—Interview with Lawrence Buchan, Cofounder of Arbutus Medical"; https://www.medgadget.com/2014/09/drilling-to-the-problem-low-cost-sterile-drill-covers-for-surgery-interview-with-lawrence-buchan-cofounder-of-arbutus-medical.html; Sep. 9, 2014; pp. 1-11.

*Primary Examiner* — Nathaniel C Chukwurah
*Assistant Examiner* — Lucas E. A. Palmer
(74) *Attorney, Agent, or Firm* — Clearpat Services, LLC; Brian D. Burkinshaw

(57) ABSTRACT

A re-usable medical procedure power tool includes a housing having a handle portion connected to a tool attachment portion and a power source portion. A removable, single use, contamination-blocking cover substantially covering the power source portion, the handle portion and the tool attachment portion. The housing has a first shape and the cover has a second shape similar to the first shape.

6 Claims, 13 Drawing Sheets

Related U.S. Application Data

(60) Provisional application No. 61/913,266, filed on Dec. 7, 2013.

(51) Int. Cl.
*B25F 5/02* (2006.01)
*A61B 46/10* (2016.01)
*A61B 50/33* (2016.01)
*A61B 50/30* (2016.01)
A61B 50/00 (2016.01)
A61B 17/00 (2006.01)

(52) U.S. Cl.
CPC ............... *A61B 50/33* (2016.02); *B25F 5/02* (2013.01); *A61B 2017/0023* (2013.01); *A61B 2050/0065* (2016.02); *A61B 2050/3008* (2016.02)

(56) References Cited

U.S. PATENT DOCUMENTS

| | | | | |
|---|---|---|---|---|
| 3,013,656 A * | 12/1961 | Murphy, Jr. | ......... | B65D 81/027 206/572 |
| 3,528,720 A * | 9/1970 | Treace | .................. | A61B 46/10 359/510 |
| 3,780,857 A * | 12/1973 | Rosano, Jr. | ............ | A61B 50/30 206/370 |
| 3,934,582 A * | 1/1976 | Gorrie | .................. | A61B 46/27 602/62 |
| 3,988,873 A | 11/1976 | Oliverius | | |
| 4,050,528 A | 9/1977 | Foltz | | |
| 4,091,880 A | 5/1978 | Troutner | | |
| 4,128,173 A * | 12/1978 | Lazarus | ............. | A61B 17/3415 206/362 |
| 4,183,613 A | 1/1980 | Walchie | | |
| 4,342,392 A * | 8/1982 | Cox | ..................... | A61F 15/001 128/855 |
| 4,359,052 A * | 11/1982 | Staub | .................... | A61B 18/10 206/363 |
| 4,440,317 A | 4/1984 | Clark | | |
| 4,522,196 A * | 6/1985 | Cunningham | ..... | A61B 1/00142 359/511 |
| 4,730,726 A * | 3/1988 | Holzwarth | ........... | B65D 81/268 206/204 |
| 4,741,326 A * | 5/1988 | Sidall | ................ | A61B 1/00091 600/123 |
| 4,825,850 A * | 5/1989 | Opie | .................. | A61B 1/0052 600/122 |
| 4,991,564 A * | 2/1991 | Takahashi | .......... | A61B 1/00142 600/123 |
| 5,168,863 A | 12/1992 | Kurtzer | | |
| 5,302,124 A * | 4/1994 | Lansing | ............... | A61C 19/004 150/154 |
| 5,359,991 A * | 11/1994 | Takahashi | .......... | A61B 1/00142 359/510 |
| 5,366,446 A * | 11/1994 | Tal | ......................... | A61B 17/34 604/180 |
| 5,379,895 A * | 1/1995 | Foslien | .................. | A61B 50/30 206/363 |
| 5,458,132 A * | 10/1995 | Yabe | .................. | A61B 1/00142 600/121 |
| 5,458,133 A * | 10/1995 | Yabe | .................. | A61B 1/00142 600/109 |
| 5,487,661 A | 1/1996 | Peithman | | |
| 5,591,119 A * | 1/1997 | Adair | ................ | A61B 1/00126 396/17 |
| 5,688,221 A * | 11/1997 | Yabe | ................ | A61B 1/00091 600/121 |
| 5,743,849 A * | 4/1998 | Rice | .................. | A61B 1/00142 600/186 |
| 5,782,821 A * | 7/1998 | Couch | .................... | A61B 46/10 383/71 |
| 5,807,107 A * | 9/1998 | Bright | .................. | A61C 19/004 433/116 |
| 5,876,328 A * | 3/1999 | Fox | ........................ | A61B 46/10 600/121 |
| 6,000,400 A | 12/1999 | Navis | | |
| 6,095,811 A | 8/2000 | Stearns | | |
| 6,309,358 B1 * | 10/2001 | Okubo | ............... | A61B 1/00142 600/466 |
| 6,350,124 B1 * | 2/2002 | Wade | ...................... | A61C 1/16 433/116 |
| 6,558,060 B1 * | 5/2003 | Raju | ..................... | A61M 25/09 401/10 |
| 6,716,215 B1 * | 4/2004 | David | ............... | A61B 17/1622 433/116 |
| 7,357,774 B2 * | 4/2008 | Cooper | .................. | A61B 46/13 600/102 |
| D610,429 S | 2/2010 | Olson | | |
| 7,728,262 B1 * | 6/2010 | Faries, Jr. | ............. | A61B 50/10 219/429 |
| 7,738,971 B2 * | 6/2010 | Swayze | ............ | A61B 17/07207 700/1 |
| 9,510,910 B2 | 12/2016 | Miller | | |
| 2002/0045802 A1 * | 4/2002 | Hascoet | ............ | A61B 1/00142 600/124 |
| 2003/0205029 A1 * | 11/2003 | Chapolini | ................ | B65B 55/02 53/449 |
| 2006/0107432 A1 * | 5/2006 | Cicero | ...................... | B25F 5/00 2/16 |
| 2006/0111723 A1 * | 5/2006 | Chapolini | ........... | A61B 17/1622 606/80 |
| 2007/0112336 A1 * | 5/2007 | Aizenfeld | ............... | A61B 10/06 606/1 |
| 2007/0112337 A1 * | 5/2007 | Salman | ............... | A61B 1/00142 606/1 |
| 2007/0270775 A1 * | 11/2007 | Miller | .................. | A61B 10/025 604/506 |
| 2007/0281272 A1 * | 12/2007 | Rahbari | .............. | A61C 3/00 433/114 |
| 2008/0045857 A1 * | 2/2008 | Miller | .................. | A61B 10/025 600/566 |
| 2008/0045860 A1 * | 2/2008 | Miller | .................. | A61B 10/025 600/567 |
| 2008/0045861 A1 * | 2/2008 | Miller | .................. | A61B 10/025 600/567 |
| 2008/0045965 A1 * | 2/2008 | Miller | .................. | A61B 10/025 606/80 |
| 2008/0195128 A1 * | 8/2008 | Orbay | ............... | A61B 1/00048 606/170 |
| 2008/0213721 A1 * | 9/2008 | Euvrard | ................ | A61C 1/16 433/116 |
| 2008/0221580 A1 * | 9/2008 | Miller | .................. | A61B 10/025 606/80 |
| 2009/0093677 A1 * | 4/2009 | Smith | ................ | A61B 17/3209 600/114 |
| 2009/0176185 A1 * | 7/2009 | Chen | ................ | A61B 1/00052 433/29 |
| 2009/0194446 A1 * | 8/2009 | Miller | ................ | A61B 10/025 206/438 |
| 2011/0017801 A1 * | 1/2011 | Zemlok | ............ | A61B 17/07207 227/175.1 |
| 2011/0033137 A1 * | 2/2011 | Gaynor | ..................... | A61L 2/00 383/105 |
| 2011/0082387 A1 * | 4/2011 | Miller | ................ | A61B 17/1637 600/567 |
| 2011/0125138 A1 * | 5/2011 | Malinouskas | ........ | A61B 17/068 606/1 |
| 2012/0061262 A1 * | 3/2012 | Merboth | ................ | A61B 50/30 206/204 |
| 2013/0095227 A1 * | 4/2013 | Bengtson | ..................... | B05D 5/00 427/2.3 |
| 2013/0184704 A1 * | 7/2013 | Beardsley | ............. | A61B 18/14 606/41 |
| 2013/0184730 A1 * | 7/2013 | Beardsley | ........ | A61B 17/07207 606/174 |
| 2013/0256120 A1 * | 10/2013 | Chao | ................... | C23C 14/0688 204/192.15 |

(56) References Cited

U.S. PATENT DOCUMENTS

| | | | |
|---|---|---|---|
| 2014/0052135 A1* | 2/2014 | Aman | A61B 17/16 606/79 |
| 2014/0121569 A1* | 5/2014 | Schafer | A61B 18/04 601/3 |
| 2015/0100066 A1* | 4/2015 | Kostrzewski | A61B 34/30 606/130 |
| 2015/0196363 A1* | 7/2015 | Aman | B25F 5/02 53/425 |
| 2015/0202009 A1* | 7/2015 | Nussbaumer | A61B 46/27 128/856 |
| 2016/0008080 A1 | 1/2016 | Beardsley | |
| 2016/0095585 A1 | 4/2016 | Zergiebel | |
| 2016/0106401 A1* | 4/2016 | Beardsley | A61B 17/00 606/1 |
| 2016/0192989 A1* | 7/2016 | Aman | A61B 17/1622 606/53 |
| 2016/0278738 A1 | 9/2016 | Buchalter | |
| 2016/0310134 A1 | 10/2016 | Contini | |
| 2017/0027658 A1* | 2/2017 | Black | A61B 50/30 |
| 2017/0055965 A1* | 3/2017 | Flatland | A61B 10/0266 |
| 2017/0196645 A1* | 7/2017 | Ozkarsli | A61C 1/16 |
| 2017/0202487 A1* | 7/2017 | Casey | A61B 5/1126 |

FOREIGN PATENT DOCUMENTS

| | | |
|---|---|---|
| CN | 201572196 U | 9/2010 |
| EP | 2851033 A2 | 3/2015 |
| JP | H0760835 | 3/1995 |
| WO | WO9806144 A1 | 2/1998 |
| WO | WO0167970 A1 | 9/2001 |

* cited by examiner

LIMITED USE TOOL DISPOSABLE ENCLOSURE

This is a Continuation of Non-Provisional Application No. 14/551,080 filed Nov. 24, 2014, which is related to and claims priority to Provisional Application No. 61/913,266 filed Dec. 7, 2013.

BACKGROUND

This disclosure relates generally to limited use power tools and more particularly to an enclosure for such tools during use in medical procedures; the enclosure being removed and discarded during reprocessing of the tools for subsequent re-use.

Important factors for any surgical instrument include sterility, cost of acquisition, maintenance, and reliability during use in the surgical suite. Each of these factors can have a significant impact on the cost of medical care for both the patient and the provider.

In recent years, there has been significant focus on the ever increasing cost of medical care. These cost increases have led to skyrocketing insurance premiums, reduced coverage, reduced reimbursements, increased fees for services, severe reductions in services for some patient groups by some providers, and unfortunately an apparent increase in infections and medical mishaps.

In an effort to reduce costs and improve profitability, both service providers and medical device suppliers are continuously looking for ways to streamline procedures, reduce time, cost, and risk from their products and services without reducing the quality of the products or services they provide to their customers. One area to benefit from these savings and improvements has been in the orthopedic surgical field through the use of high precision, battery powered surgical instrumentation. In the late 1960's and early 1970's battery operated drills were bulky, ill-balanced and required multiple batteries to perform some surgeries due to the limited energy storage capacity and poor efficiency of the electric motors.

Since then, manufacturers have attempted to make batteries more efficient with higher energy storage capacity, reduced size, and improved rechargeable lifespans. Likewise, motor housings such as saw and drill bodies have become more ergonomic, balanced, lightweight and energy efficient. As with many standard hand tools having multiple moving components, instrument manufacturers have reduced weight by utilizing lighter materials such as plastic housings, and gears, and put weight reducing apertures in what were previously solid housings. In some cases, standard mountings for attachments have been replaced with modular fittings, allowing for greater interchangeability and component selections. Additionally, manufacturers have attempted to improve electrical components by upgrading them with more modern components wherever possible.

All of these improvements in equipment construction have improved efficiencies, costs and quality in some areas while at the same time increasing costs for acquisition, maintenance and increasing risks in other ways that were not previously seen or predicted. Often times cost and quality can be inversely proportional to one another. One example of the increased cost and patient risk is seen in the cleaning and maintenance of instruments.

Recent published reports suggest that many of the surgical instruments used in operations were not being cleaned and/or sterilized appropriately in the very hospital facilities that were established and tasked for that purpose. In numerous reports, following cleaning and sterilization, it was noted that upon closer secondary inspection, the inside of small diameter cannulas and intricate mini-components of arthroscopic shavers that are used for many of today's minimally invasive procedures, contained human tissue and bone fragments from previous surgeries. In other cases, modular components of drills and saws such as chucks, drill bits and blades were found to have similar debris or pieces of cleaning brushes and/or bristles embedded in or on them. These investigations have demonstrated that in most cases the instruments were not cleaned according to manufacturer's specifications which has likely lead to many documented cases of serious, multiple, serial infections for subsequent patients. A pilot program conducted by the Centers for Medicare and Medicaid Services (Schaefer et al., 2010; JAMA 2010; 303(22):2273-2279) inspected 1500 outpatient surgery centers and found that 28% had been cited for infectious control deficiencies associated with equipment cleaning and sterilization. The costs to the patients and the hospitals in both expense and liability to deal with these infections can be and has been staggering.

In other cases, critical battery-operated, motorized tools such as drills or bone saws have ceased to function due to dead batteries that no longer maintain their capacity to hold a charge, or due to internal part failure, often attributable to overuse or lack of proper maintenance. The resultant downtime in the operating suite is extremely costly, as the procedure step must be put on hold while replacement or substitute tools are obtained. Wait times may often exceed 20-30 minutes, resulting in additional anesthesia exposure for the patient, additional operating room time (charged to the patient) and potential delays to other procedures where the replacement or substitute equipment had been scheduled for use in a later procedure. Recent estimates (2005) establish the average cost of operating room time to range between $62/min. (range $21.80-$133.12) depending on the procedure. These figures did not include extra resources provided by the hospital for special, non-routine situations which often occur during standard procedures, and did not include the surgeon and anesthesia provider fees, (anesthesia fees are estimated to be $4/min; range $2.20-$6.10).

Hospitals and instrument manufacturers are continuously attempting to find improved ways to reduce risk associated with infection in general, and more recently, specifically from improperly cleaned instruments. One approach has been to use more disposable, single-use instruments such as drills, saw blades and plastic cannulas. Additionally, many laparoscopic devices such as, surgical staplers and trocars, are designed as single use items that are intended to be immediately disposed of after use. Unfortunately, at today's acquisition costs, the total cost of ownership and benefits are not always clear for high-use battery-operated, motorized instruments such as saws, drills and reamers used in orthopedic procedures and the idea of disposable powered instruments has not been readily embraced.

A recent trend in the medical community is reprocessing of single use medical instruments, by parties other than the original equipment manufacturer, instead of discarding them after use. During reprocessing, the medical instruments are disassembled, cleaned and sterilized. They are then reassembled for future use. However, because the medical instruments reprocessed for further use are specifically provided for use during a single procedure, the performance of the medical instruments tends to decline after reprocessing, because the components making up the medical instrument are not adapted for multiple uses and will degrade in performance when used beyond their intended life span. For example, reprocessing of the cutting devices on trocars is intended to extend these devices beyond their intended mission life, but often results in duller cutting edges on the blades because neither the materials used nor the reprocessing method can restore the device to the original manufacturing specifications. A greater force, therefore, is needed to make an initial incision, causing more trauma to the patient. In addition, the use of greater force increases the potential for error during the surgical procedure.

Most hospitals and surgery centers buy high-use, reusable motorized, pneumatic, wired or battery operated, orthopedic surgical equipment and are expected to clean, sterilize, and maintain them internally within the hospital. Unfortunately, the technicians hired to perform this work are typically not qualified or trained to perform this work adequately for the many varieties of powered instruments used. Further, manufacturers rarely provide the hospital/client with the training or diagnostic equipment necessary to evaluate or test the equipment. Often times the hospital employees responsible for cleaning and maintenance are not technicians at all, being paid slightly more than minimum wage, working at a fast pace to merely wash, count, and reload instruments into their appropriate system trays and flash sterilize them as quickly as possible, in an effort to keep the equipment in rotation in the hospital operating rooms, where higher throughput dictates profitability for the hospital or surgery center.

As a result of high throughput requirements, general maintenance is rarely done and preventative monitoring and maintenance is almost never done on this type of equipment. Hospital budgets for internal maintenance of equipment are generally geared toward high-end, multi-million dollar capital equipment such as x-ray and radiological equipment. It is generally assumed that it is faster, simpler, and more economical for the hospital to wait for hand-held instruments, such as drills, saws and reamers to fail, then, send them back to the manufacturer for repair or replacement.

Thus it has become apparent that there is a need for an improved system of cost-effective, battery-operated, motorized tools in conjunction with better cleaning and maintenance protocols which can provide the hospital, surgeon, and most importantly, the patient, with a higher degree of efficiency and cleanliness while reducing risk and keeping the costs of cleaning, maintenance, and repair as low as possible.

SUMMARY

Accordingly, a reusable medical procedure power tool includes a housing having a handle portion connected to a tool attachment portion and a power source portion. A removable, single use, contamination-blocking cover substantially covering the power source portion, the handle portion and the tool attachment portion. The housing has a first shape and the cover has a second shape similar to the first shape.

DETAILED DESCRIPTION

Figure 1:
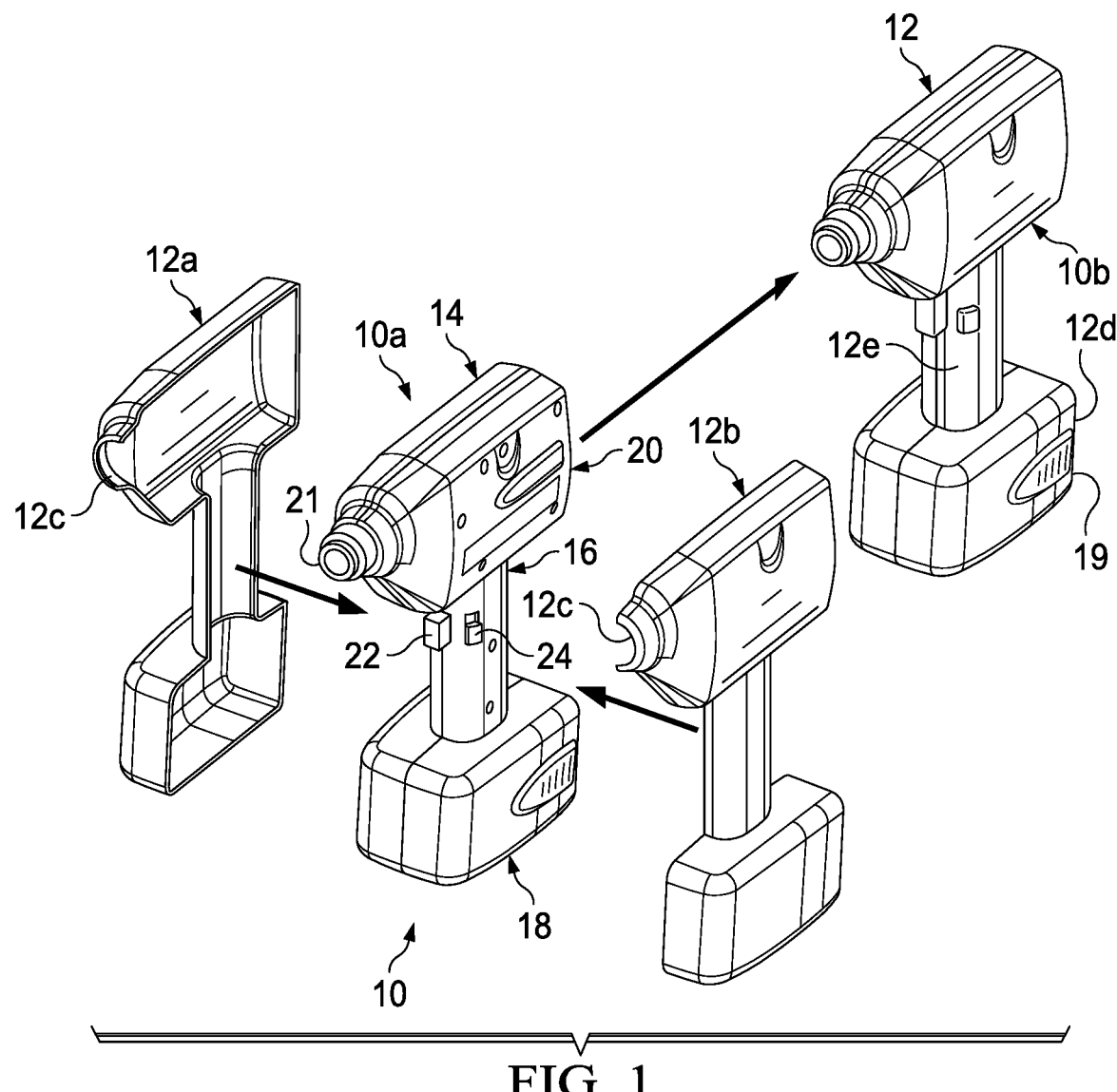
FIG. 1 is a perspective, assembly view illustrating an embodiment of a power tool having a housing and a removable, single use, hardshell or softshell wrap or cover formed of a contamination blocking material.

The embodiment of FIG. 1 illustrates an exemplary power tool 10 for use in medical procedures such as surgical procedures. A removable, single use, contamination-blocking cover 12 is provided for blocking excessive contamination of the power tool 10 during use. The cover 12 is replaceable, e.g. after the procedure, the cover 12 may be removed and replaced by a new cover 12.

The tool 10 includes a housing 14 comprising a handle portion 16 and in this example, a power source portion such as a receiver 18 for a portable battery pack and a tool attachment portion 20 having a chuck 21 provided for releasably receiving and holding an attachment tool such as a drill bit or a saw blade. The handle 16 includes a control portion including but not limited to an actuating trigger 22, a trigger lock 24 and a forward-reverse switch, all of which may not be visible in FIG. 1. The attachment point of a saw blade may vary depending on whether it is a reciprocating or oscillating blade.

The cover 12 preferably includes a two-piece hard or soft outer shell including portions 12a and 12b. The tool 10 is illustrated at 10a prior to application of the cover 12, and is illustrated at 10b after application of the cover 12. A first opening 12c is provided in cover 12 adjacent chuck 21 when the cover is applied to the tool 10. A second opening 12d, which may be closed by a sealable door 19, is provided in power source portion 18. Regardless of the material used for the cover 12, a flexible portion 12e of the cover 12 is provided on the handle 16 to provide a user with a tactile feel and operable movement of for example, the trigger 22 and the trigger lock 24.

The replaceable cover 12 is applied to tool 10 by a tool re-processor. Once the tool 10 is used in a procedure, the cover has become contaminated along with portions of the tool 10 which are adjacent the openings 12*c*, 12*d*. The tool 10, including cover 12, is returned to the tool re-processor where the cover 12 is removed and discarded. The tool 10 is then cleaned and a new cover 12 is mounted on the tool 10, rendering the tool 10 ready for re-use.

Figure 2:
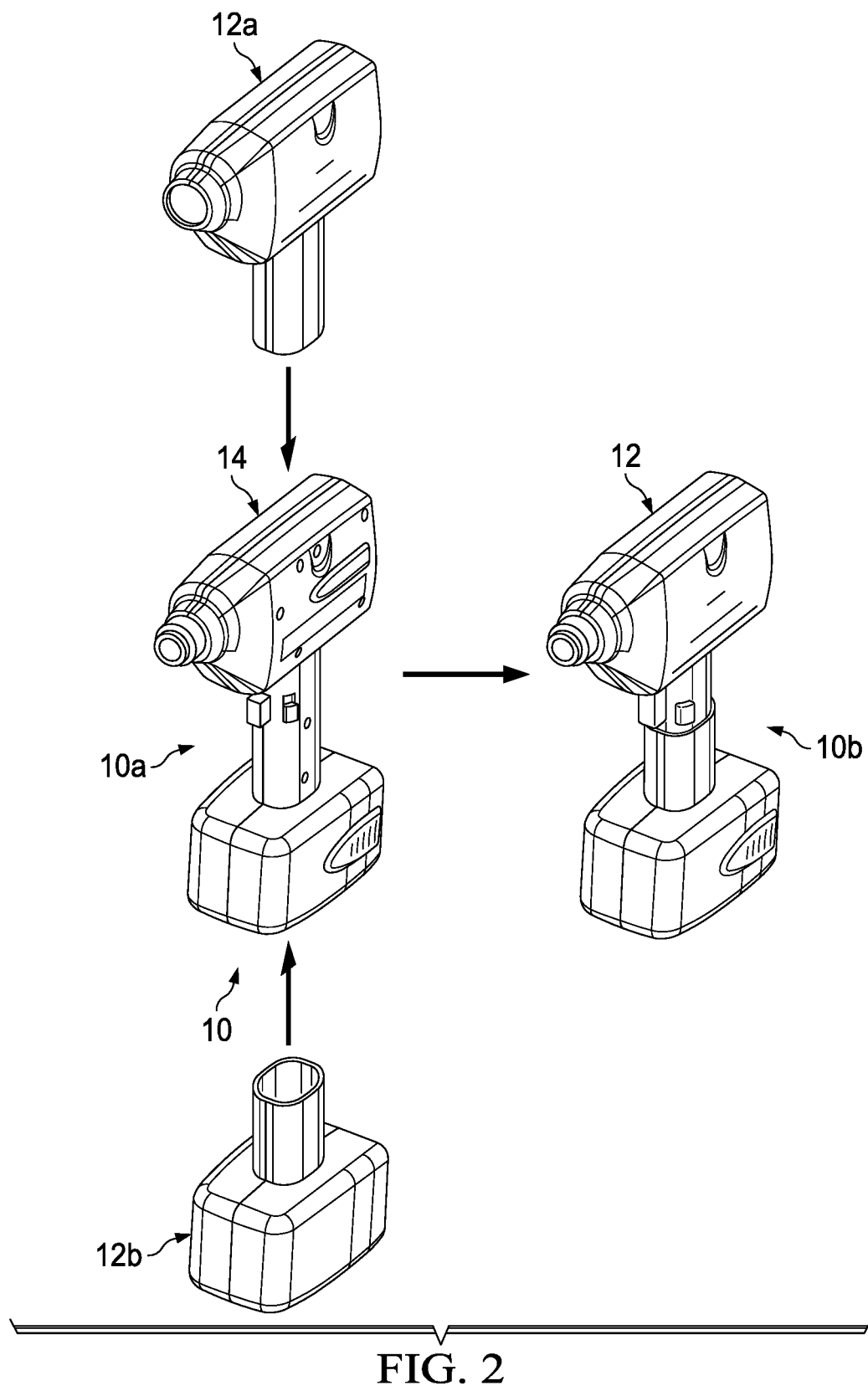
FIG. 2 is a perspective assembly view illustrating an embodiment of the power tool of FIG. 1 wherein the cover is a stretch membrane.
Figure 3A:
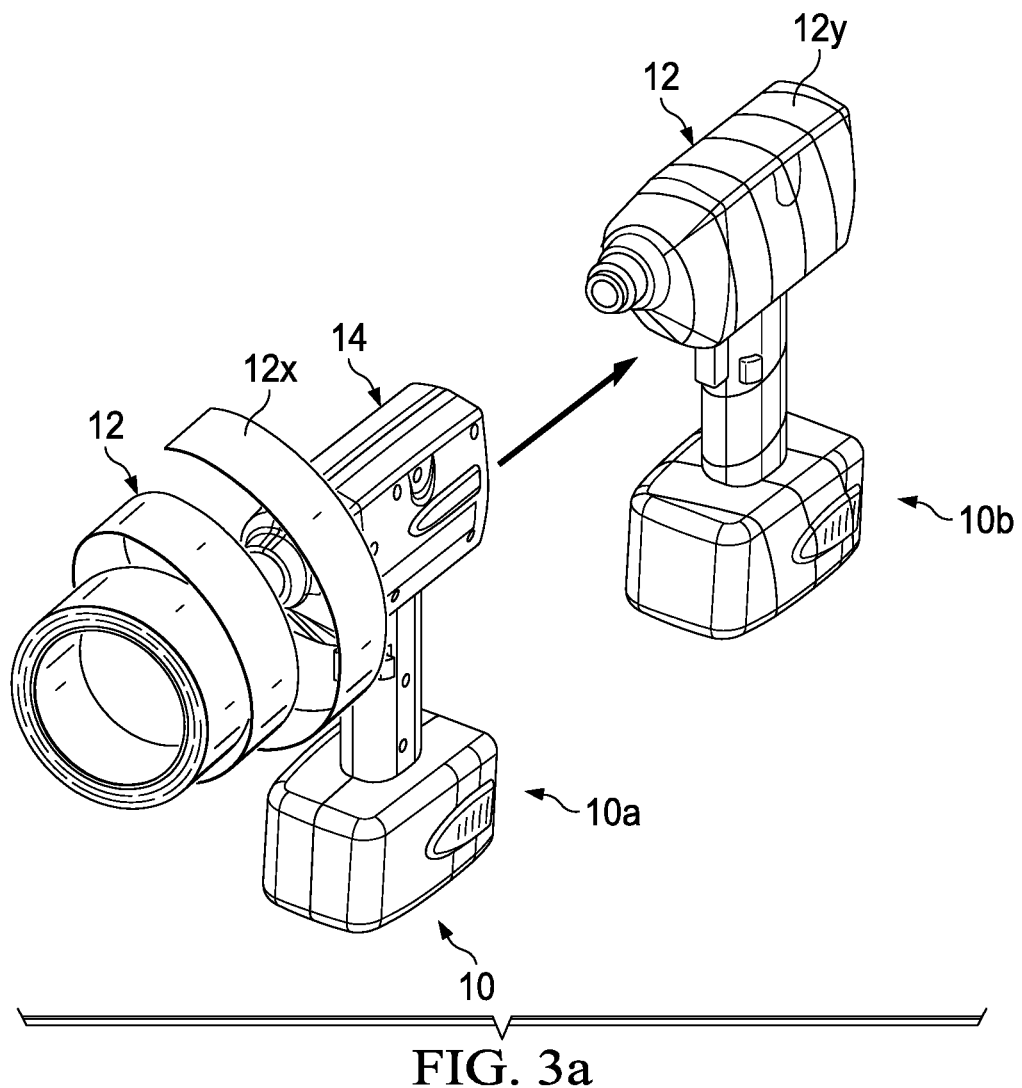
FIGS. 3a and 3b are perspective assembly views illustrating embodiments of the power tool of FIG. 1 wherein the covers include a shrink-wrap tape and a shrink-wrap tube respectively.
Figure 3B:
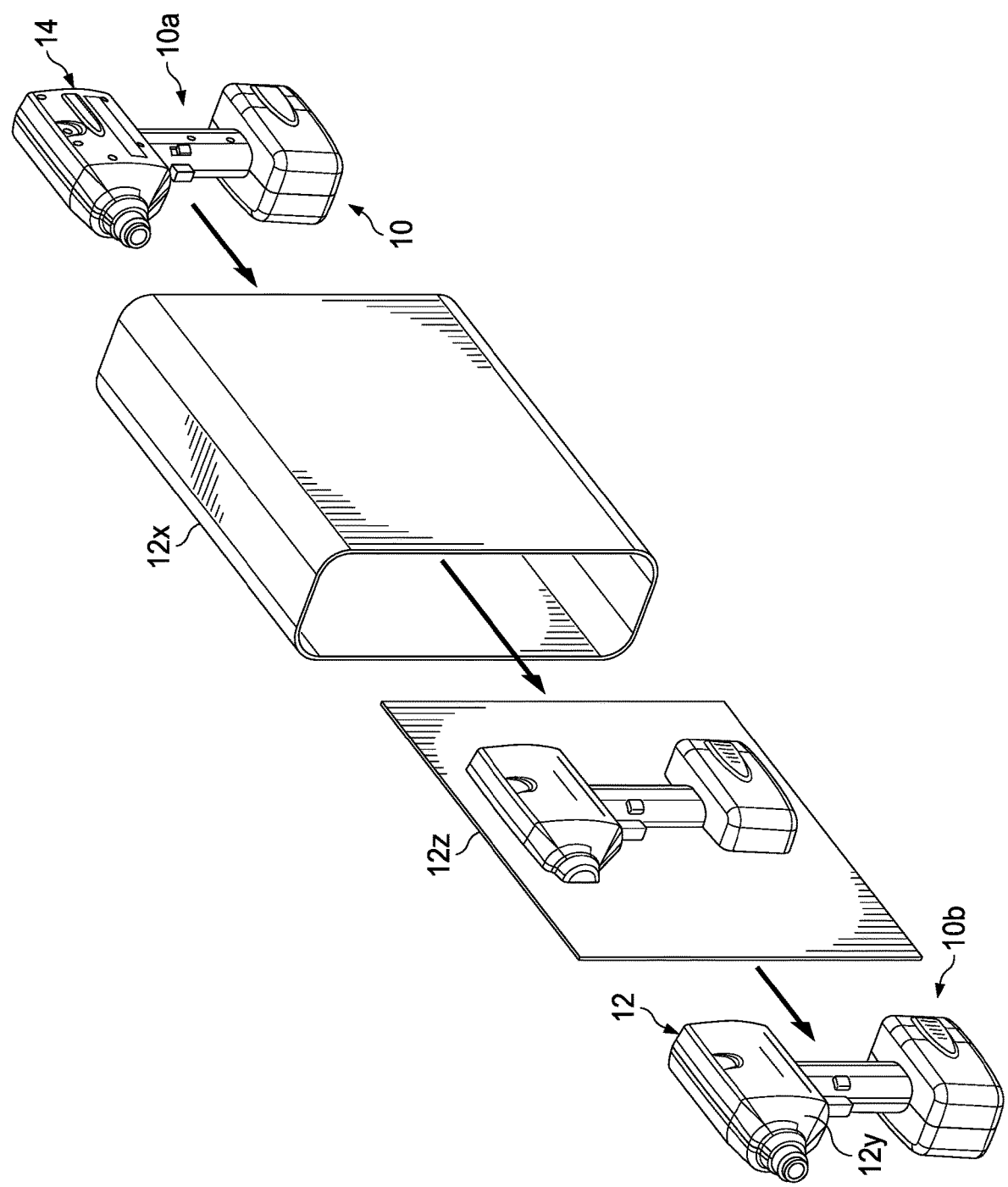
Figure 4:
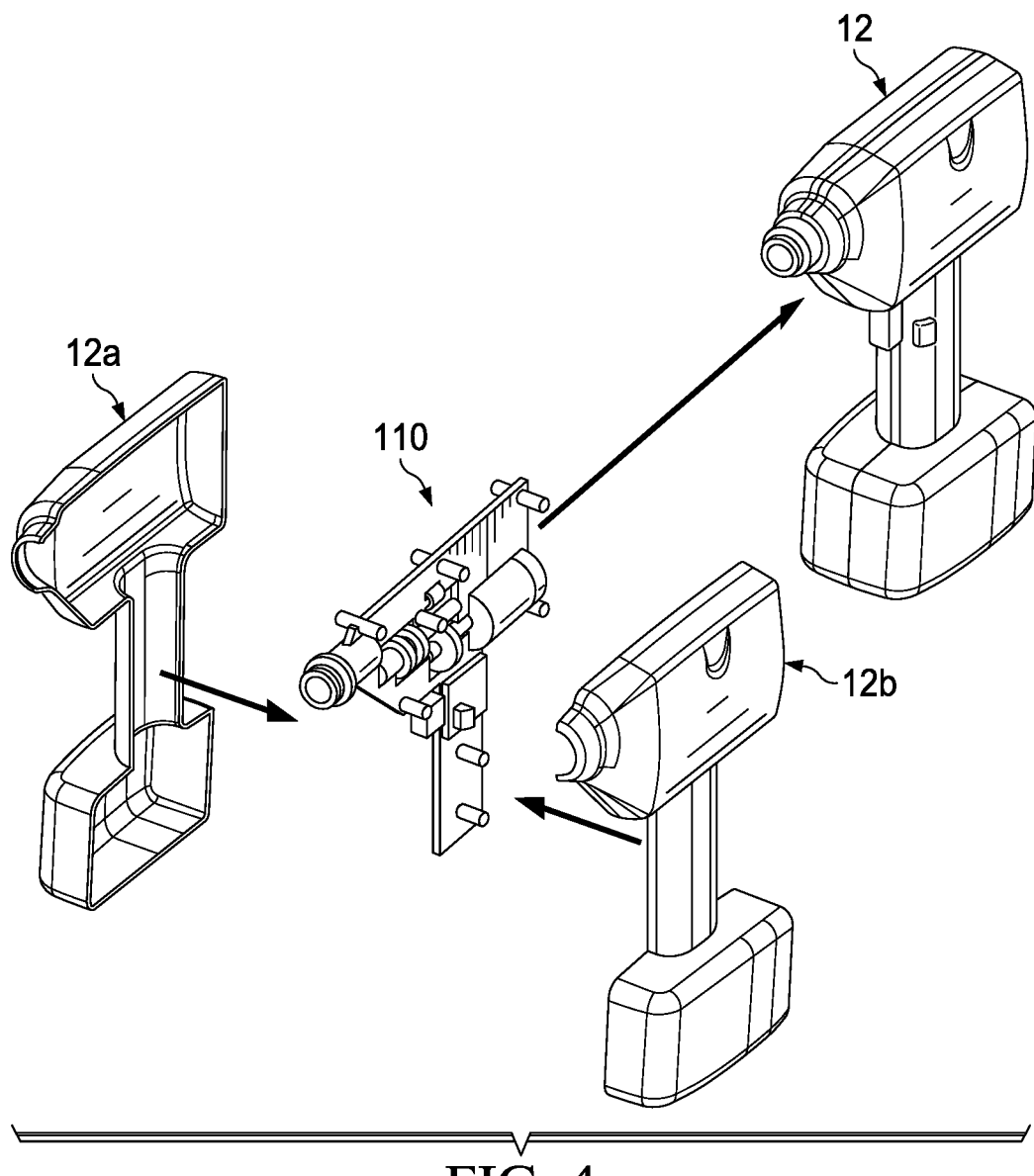
FIG. 4 is a perspective assembly view illustrating an embodiment of a mechanical sub-frame of a power tool having no housing and wherein the cover is a disposable hardshell.
Figure 5:
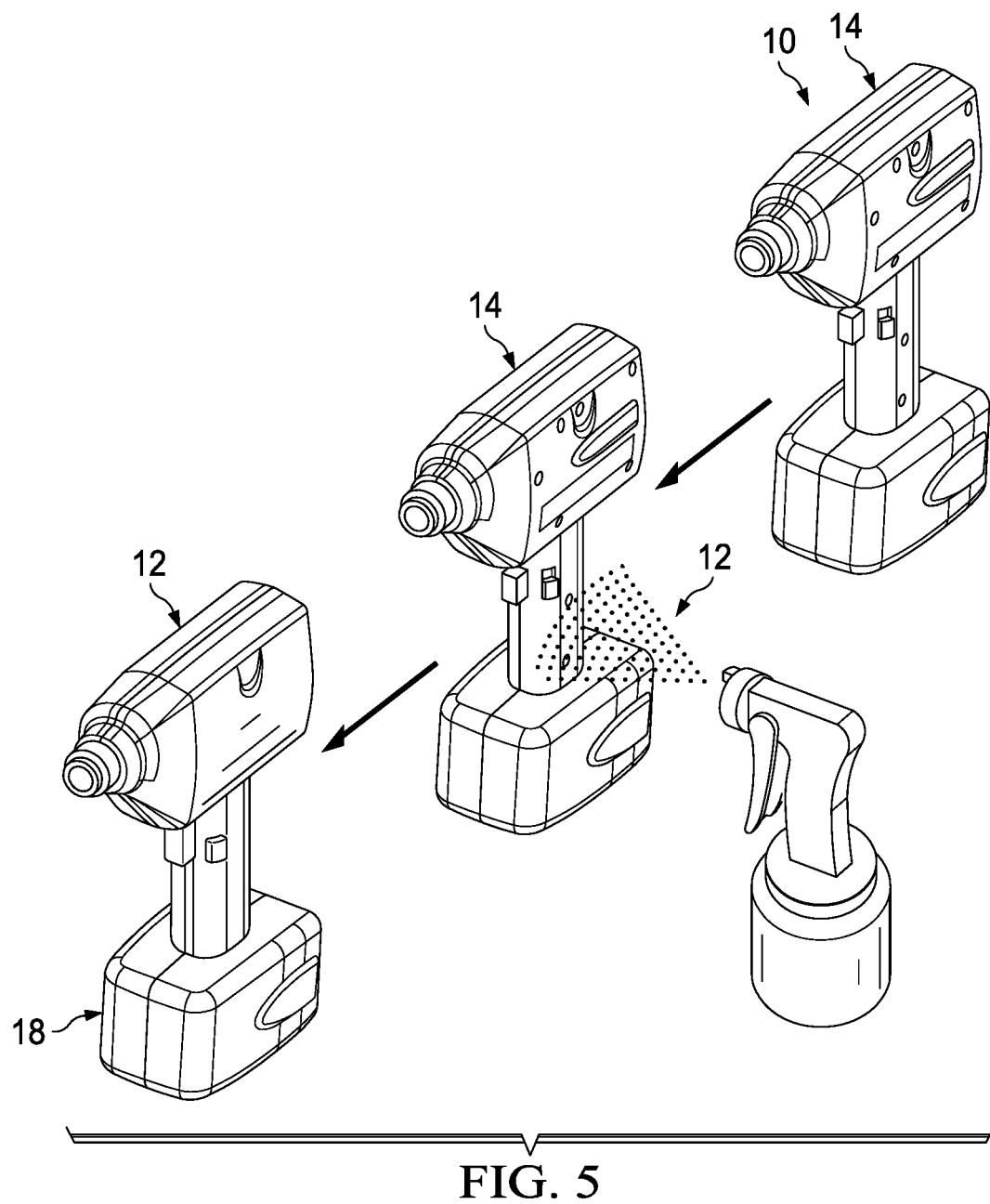
FIG. 5 is a perspective assembly view illustrating an embodiment of the power tool of FIG. 1 wherein the cover is spray-on applied.
Figure 6:
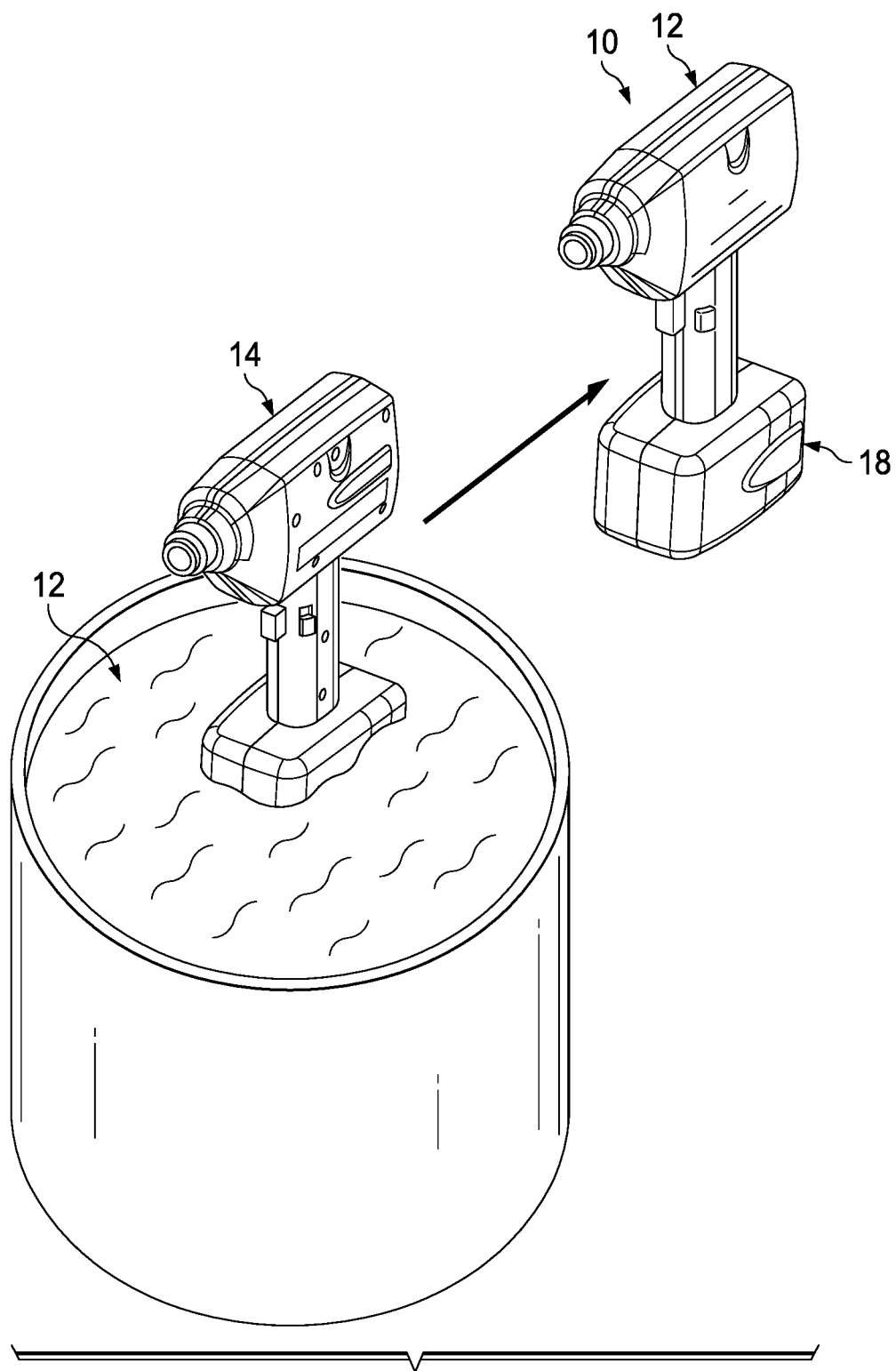
FIG. 6 is a perspective assembly view illustrating an embodiment of the power tool of FIG. 1 wherein the cover is dip applied.
Figure 7:
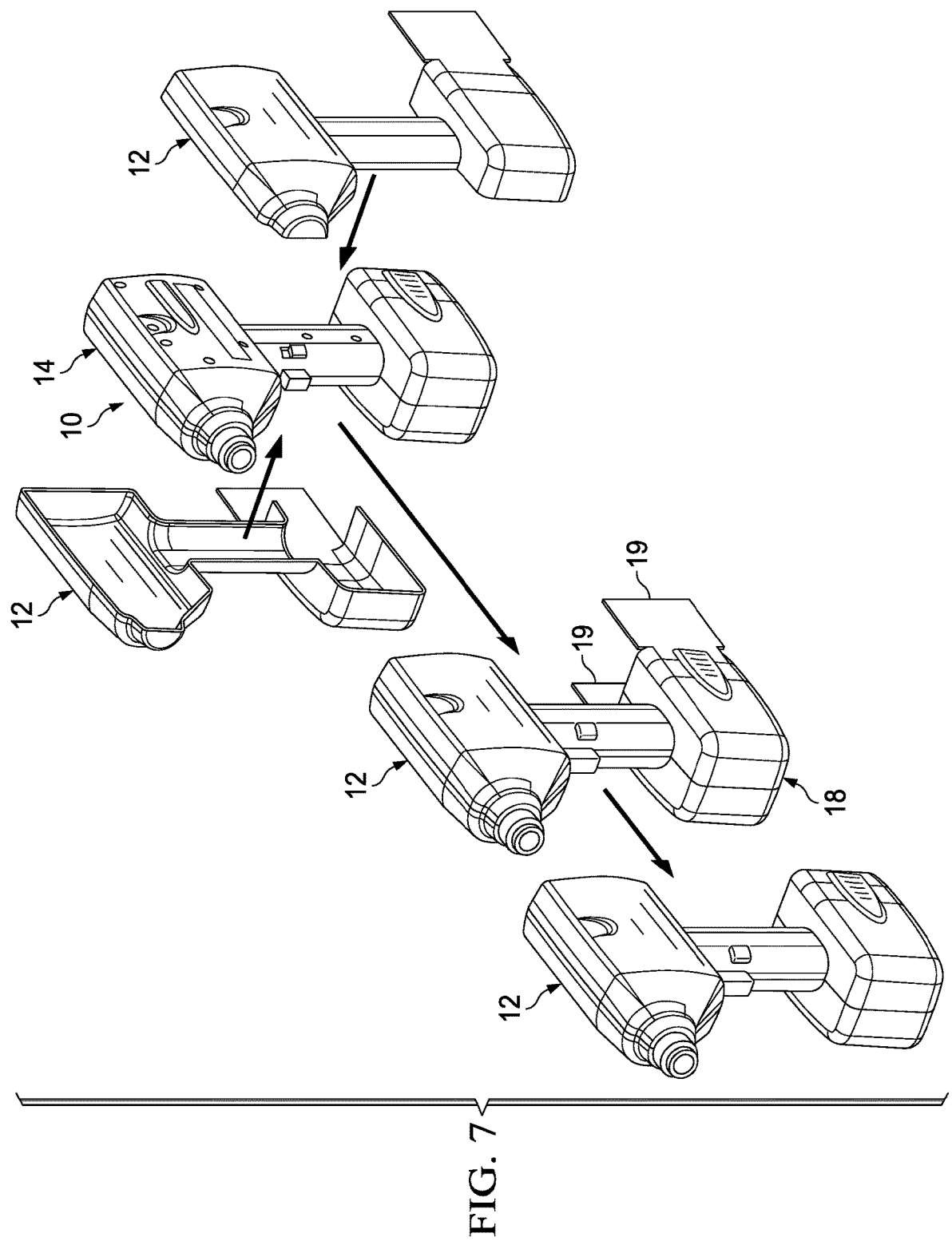
FIG. 7 is a perspective assembly view illustrating an embodiment of the power tool of FIG. 1 wherein the cover is a header bag.
Figure 8:
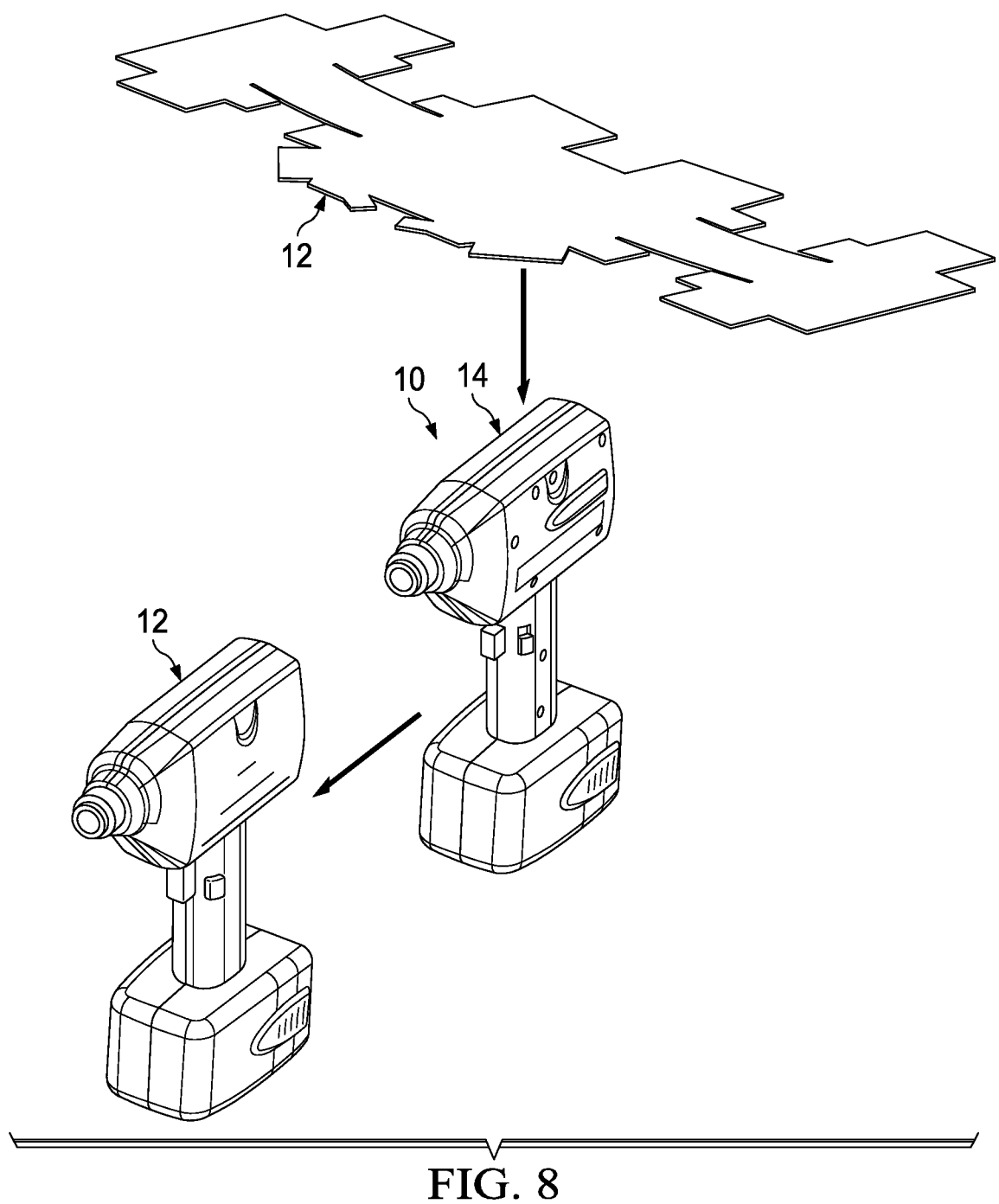
FIG. 8 is a perspective assembly view illustrating an embodiment of the power tool of FIG. 1 wherein the cover is a pre-cut wrap.
Figure 9:
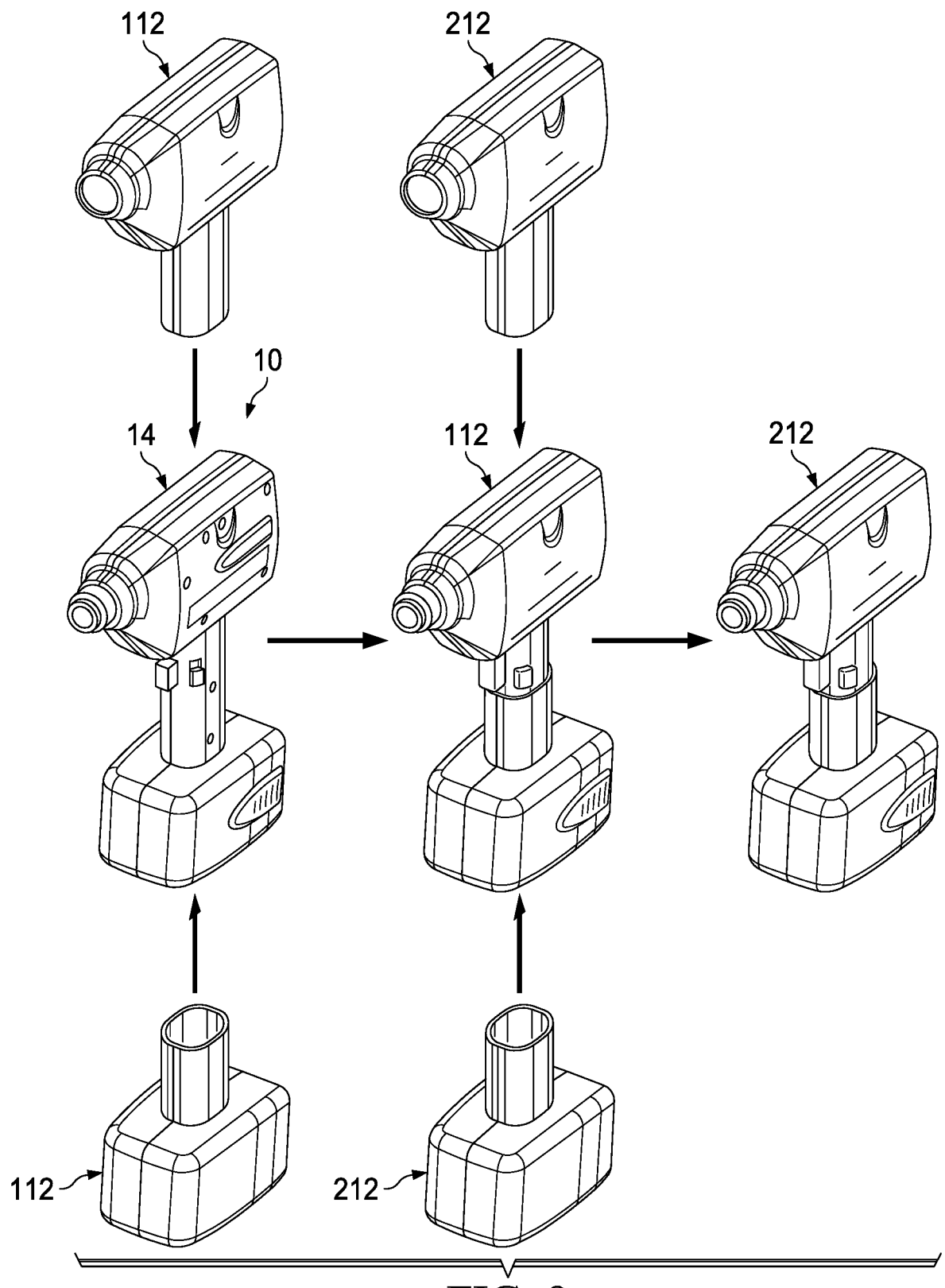
FIG. 9 is a perspective assembly view illustrating an embodiment of the power tool of FIG. 1 wherein the cover is double layer stretch membrane.

More specific information regarding the tool 10 and cover 12 of the FIG. 1 embodiment as described above are set forth below as follows:

a. Existing product or new product uses a rigid body mechanical housing 14 in conjunction with either a hard or soft/flexible shell outer shield 12 that covers and protects the majority of the tool 10 from contamination by blood/bone/tissue during a procedure. Combinations of materials such as a hard shell with flexible inserted areas for controls actuation are also contained in this area. Additional reinforcements or seals can be used in high stress areas.
     i. Materials and alloys/laminates of these materials appropriate for this concept include but are not limited to:
       a. PETG & A/PET
       b. Polystyrene
       c. Acrylic
       d. Polycarbonate
       e. ABS
       f. Nylon
       g. Polyolefin
       h. Polyetheretherketone PEEK
       i. Polyetherimide PEI
       j. Polyetersulfone PES
       k. Polyvinylidene PVDF
       l. Polymethylpentene PMP
       m. Polysulfone PSO
       n. Ethylene-chlorotrifluoroethylene ECTFE
       o. Metals
     ii. Soft/flexible outer shell can be produced using injection molding, thermoforming, dip molding, compression molding or other processes. Materials and alloys of these materials appropriate for this concept include but are not limited to:
       a. Synthetic Paper
       b. C-Flex
       c. Flexible PVC
       d. Polycarbonate
       e. Polyester
       f. Polyethylene
       g. Polypropylene
       h. Nylon
       i. Polyolefin
   b. Methods appropriate for fastening the outer shell to/around the inner structure include but are not limited to:
     i. Fasteners such as:
       1. Screws
       2. Rivets
       3. Bolts
     ii. Molded features such as:
       1. Clips
       2. Press fits
       3. Slip fits
     iii. Adhesive in multiple forms
       1. Tape
       2. Glue
       3. Pressure sensitive adhesive
       4. Hot melt adhesives
       5. Contact adhesives
     iv. Secondary operations
       1. Heat Seal
       2. Pierce Several further embodiments are described below. More specific information regarding the tool 10 and a stretch membrane cover 12 including upper member 12*a* and lower member 12*b,* of the FIG. 2 embodiment is described below as follows:

a. This embodiment uses a rigid body mechanical housing 14 in conjunction with a highly stretchable membrane 12 (balloon like) to cover and protect the tool 10 from contamination by blood/bone/tissue during a procedure. This cover 12 is a removable, single use cover of contamination blocking material. Single and multiple layer configurations can be considered for this version. Single or multiple membranes may be used to protect various areas of the tool 10 (main body vs. battery pack allowing access to battery pack at the start of a procedure). Variable wall thickness or reinforcements can be used in high stress areas. Members 12*a* and 12*b* are stretched over housing 14 and combined to form cover 12. Tool 10 is shown at 10*a* prior to application of cover 12, and is shown at 10*b* after the application of cover 12.
     i. Flexible membranes can be produced using blow molding, dip molding, thermoforming, or other processes. Members 12*a* and 12*b* are stretched over housing 14 and combined to form cover 12. Tool 10 is shown at 10*a* prior to application of cover 12, and is shown at 10*b* after the application of cover 12.
       1. Materials and alloys of these materials appropriate for this concept include but are not limited to:
         a. Silicone
         b. Latex Rubber
         c. Synthetic Rubber
         d. Polychloroprene
         e. Flexible PVC
   b. Methods appropriate for applying the membrane around the outer shell include but are not limited to:
     i. Stretching:
       1. Manually
       2. Automated
       3. Individual sections (i.e. main body separate from Battery Pack area)
     ii. Secondary operation:
       1. Additional seals/retention elements at operation interfaces such as drill chuck or saw adaptor
       2. Additional tape reinforcements in high stress areas More specific information regarding the tool 10 and a shrink wrap cover 12, FIGS. 3*a*, 3*b*, is described below as follows:

a. This embodiment uses a rigid body mechanical housing 14 in conjunction with a secondary shrink-wrap element 12 to cover and protect the device from contamination by blood/bone/tissue during a procedure. Cover 12 is a removable, single-use cover of contamination blocking material. Single and multiple layer configurations can be considered for this version (see considerations for transport as non-biohazard state). Single or multiple wraps may be used to protect various areas of the tool 10 (main body vs. battery pack allowing access to battery pack at the start of a procedure). Additional reinforcements or seals can be used in high stress areas. Shrink methods can include both heat application or a chilling operation depending on the type of shrink wrap utilized. Tool 10 is shown at 10*a* prior to application of cover 12, and is shown at 10*b* after the application of cover 12 and shrink activation, FIGS. 3*a*, 3*b*.
     i. Flexible shrink-wrap can be produced using extrusion processes, and are available in tape, FIG. 3*a*, sheet or tube form, FIG. 3*b* and can be either heat or cold activated to create the wrap required for device isolation. Some tape applications carry an adhesive layer. The shrink-wrap tube cover 12x, FIG. 3b, is trimmed at 12y after shrink activation at 12z. Shrink-wrap tape, FIG. 3a is shown prior to wrapping at 12x and after wrapping and shrink activation at 12y.
1. Materials and alloys/laminates of these materials appropriate for this concept include but are not limited to:
   a. Acetate
   b. Polyethylene
   c. PVC
   d. Polyester
   e. Polyolefin
   f. Polypropylene
b. Methods appropriate for applying the membrane around the outer shell include but are not limited to:
   i. Tape Wrapping:
      1. Manually
      2. Automated
      3. Individual sections (i.e. main body separate from Battery Pack area)
   ii. Film Wrap:
      1. Manually
      2. Automated
      3. Individual sections (i.e. main body separate from Battery Pack area)
   iii. Secondary operations:
      1. Heat seal for complex geometries
      2. Shrink Tunnel
      3. Heat Gun
      4. Refrigeration
      5. Additional tape reinforcements in high stress areas
      6. Adhesive application to tape wrap In FIG. 4, an embodiment utilizes no traditional housing 14, as described above, but provides the inner frame and working parts as tool 110 and the outer hard shell cover 12 of tool 110 is provided as a disposable cover, as described below:
   a. This embodiment uses a rigid sub-frame 110 carrying all mechanical components. The hard shell cover 12 has minimal mechanical content and is used as a disposable single-use housing of a contamination blocking material to protect the mechanical components from contamination by blood / bone / tissue during a procedure. Cover 12 comprises cover portions 12a, 12b. The sub-frame and mechanical components are intended for multiple re-use. This configuration may also be used in conjunction with a soft/flexible outer shell allowing for return of the device in a non-biohazard state. Combinations of materials such as hard shell with flexible inserted areas for controls actuation are also contained in this area.
Additional reinforcements or seals can be used in areas subject to contaminant intrusion. Thus, the hard shell, single-use disposable cover 12 functions as a combination previously provided by a traditional housing 14 and cover 12.
   i. Hard outer shell can be produced using injection molding, thermoforming, or other processes.
      I. Materials and alloys/laminates of these materials appropriate for this concept include but are not limited to:
         a. PETG & A/PET
         b. Polystyrene
         c. Acrylic
         d. Polycarbonate
         e. ABS
         f. Nylon
         g. Polyolefin
         h. Polyetheretherketone PEEK
         i. Polyetherimide PEI
         j. Polyetersulfone PES
         k. Polyvinylidene PVDF
         l. Polymethylpentene PMP
         m. Polysulfone PSO
         n. Ethylene-chlorotrifluoroethylene ECTFE
         o. Metals
   b. Methods appropriate for fastening the outer shell to/around the inner structure include but are no limited to:
      i. Fasteners such as:
         1. Screws
         2. Rivets
         3. Bolts
      ii. Molded features such as:
         1. Clips
         2. Press fits
         3. Slip fits
      iii. Secondary operation:
         1. Tape
         2. Glue
         3. Pressure sensitive adhesive
         4. Hot melt adhesives
         5. Contact adhesives
         6. Heat seal
         7. Pierce In FIG. 5, another embodiment includes a tool 10 having a protective spray cover 12 further described as follows:
   a. This embodiment uses a rigid body mechanical housing 14 in conjunction with a secondary spray-on protective layer 12 to cover and protect the tool 10 from contamination by blood/bone/tissue during a procedure. Single and multiple layer configurations can be considered for this version by using a release layer between subsequent spray applications. This configuration may be used in conjunction with previously described protection systems to allow access to power source portion 18 at the start of a procedure. Additional reinforcements or seals can be used in areas subject to contaminant intrusion. Layer 12 is a removable, single-use cover of contamination blocking material.
      i. Spray on protective layers can be applied either manually or automatically. Specific areas not to be coated can be masked to ensure correct device function. It may also be desirable to coat individual components prior to assembly to minimize masking issues.
         1. Materials and alloys/laminates of these materials appropriate for this concept include but are not limited to:
            a. Natural rubber
            b. Synthetic rubber
            c. Polyurethane
            d. Acrylic
            e. Polyethylene
            f. PVC
            g. Polyester
            h. Polyolefin
            i. Polypropylene
      b. Methods appropriate for applying the membrane around the outer shell include but are not limited to:
         i. Aerosol application:
            1. Manually
            2. Automated
            3. Individual section (i.e. main body separate from Battery Pack area)
         ii. Secondary operations:
            I. Drying/curing In FIG. 6, another embodiment includes a tool 10 having a protective dip layer as a cover 12 further described as follows:

a. This embodiment uses a rigid body mechanical housing in conjunction with a secondary dipping operation to apply a protective layer 12 intended to cover and protect the tool 10 from contamination by blood/bone/tissue during a procedure. Single and multiple layer configurations can be considered for this version by using a release layer between subsequent dip applications. This configuration may be used in conjunction with previously described protection systems to allow access to power source portion 18 at the start of a procedure. Additional reinforcements or seals can be used in areas subject to contaminant intrusion. Layer 12 is a removable, single-use cover of contamination blocking material.
- i. Dip protective layers can be applied either manually or automatically. Specific areas not to be coated can be masked to ensure correct device function.
  1. Materials and alloys/laminates of these materials appropriate for this concept include but are not limited to:
     a. Natural rubber
     b. Synthetic rubber
     c. Polyurethane
     d. Acrylic
     e. Polyethylene
     f. PVC
     g. Polyester
     h. Polyolefin
     i. Polypropylene
- b. Methods appropriate for applying the membrane around the outer shell include but are not limited to:
  i. Dip application:
     1. Manually
     2. Automated
     3. Individual sections (i.e. main body separate from Battery Pack area)
     4. Secondary operations drying/curing In FIG. 7, another embodiment includes a tool 10 with battery door 19 providing access to power source portion 18 and having a protective header bag formed to shape as a cover 12 further described as follows:

a. This embodiment uses a rigid body mechanical housing 14 in conjunction with a formed header bag outer shielding cover 12 that protects the majority of the tool 10 from contamination by blood/bone/tissue during a procedure. Additional reinforcements or seals can be used in high stress areas. Header bag cover 12 comprises a removable, single-use cover of contamination blocking material.
- i. Header bag cover 12 can be produced using an extrusion process for the base material with secondary forming and sealing operations to create a sealed enclosure. The header bag 12 is a shaped, non-stretchable, bag-like shell loosely fitted over the housing 14.
  1. Materials and alloys of these materials appropriate for this concept include but are not limited to:
     a. Synthetic paper
     b. C-Flex
     c. Flexible PVC
     d. Polycarbonate
     e. Polyester
     f. Polyethylene
     g. Polypropylene
     h. Nylon
     i. Polyolefin
- b. Methods appropriate for fastening the header bag to/around the inner structure include but are not limited to:
  i. Adhesive in multiple forms
     1. Tape
     2. Glue
     3. Pressure sensitive adhesive
     4. Hot melt adhesives
     5. Contact adhesives In FIG. 8, another embodiment includes a tool 10 having a protective die cut wrap as a cover 12 further described as follows:

a. This embodiment uses a rigid body mechanical housing 14 in conjunction with a Precut Wrap outer shielding cover 12 that once applied protects the majority of the tool 10 from contamination by blood/bone/tissue during a procedure. Additional reinforcements or seals can be used in high stress areas or areas vulnerable to contaminant intrusion.
- i. The device can be produced using an extrusion process for the base material with secondary cutting operations and sealing components added to provide a method for creating a sealed enclosure.
  1. Materials and alloys of these materials appropriate for this concept include but are not limited to:
     a. Synthetic paper
     b. C-Flex
     c. Flexible PCV
     d. Polycarbonate
     e. Polyester
     f. Polyethylene
     g. Polypropylene
     h. Nylon
     i. Polyolefin
- b. Methods for cutting the wrap to conform to the device include but are not limited to:
  i. Manual cutting
  ii. Die cutting
  iii. Rotary cutting
- c. Methods appropriate for securing the wrap to/around the device include but are not limited to:
  i. Creation of appropriate flattened geometry that once wrapped conforms to the geometry of the device.
  ii. Adhesive in multiple forms:
     1. Tape
     2. Glue
     3. Pressure sensitive adhesive
     4. Hot melt adhesives
     5. Contact adhesives In FIG. 9, similar to FIG. 2, another embodiment discloses a power tool 10 including a first inner stretch membrane cover 112 and a second outer stretch membrane cover 212. This embodiment adds the outer cover 212 so that after use of the tool 10, the outer cover 212 is removed and the inner membrane 112 stays in place on the tool 10. This embodiment enables shipping the used tool to a re-processor so as to avoid shipping a biohazard product. This embodiment is further described as follows:

a. This embodiment uses a rigid body mechanical housing 14 in conjunction with a two layer soft / flexible shell outer cover 112 and 212 that protects the majority of the device from contamination by blood/bone/tissue during a procedure. Following the procedure and before return shipment of the device the outermost contaminated cover 212 is removed presenting the inner cover 112 that is a non-biohazard product and can economically be returned for re-processing.

Figure 10:
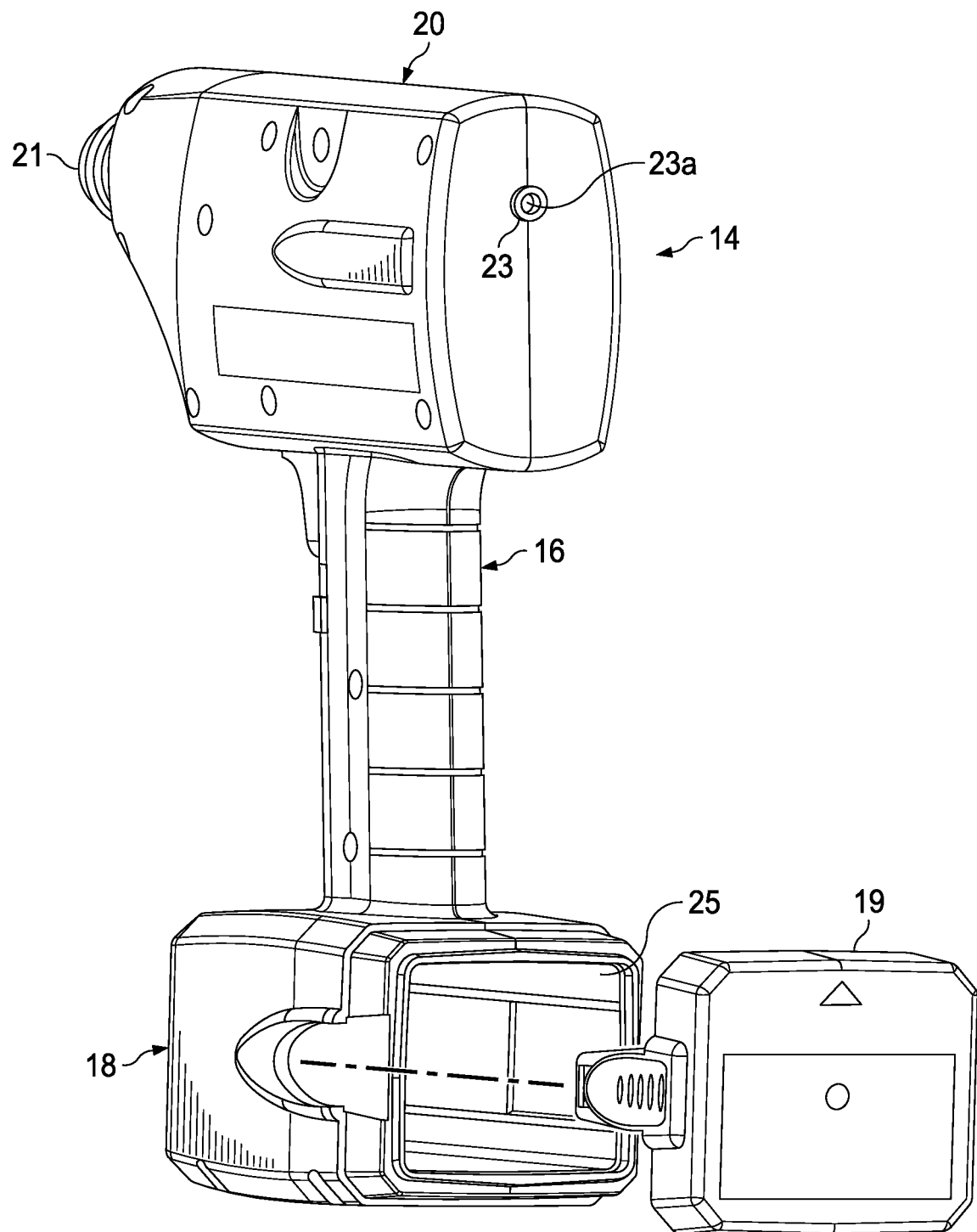
FIG. 10 is a perspective view illustrating an embodiment of the power tool housing as viewed from the backside of the tool and having a sealable door removed to expose a cavity to receive a portable battery.
Figure 11:
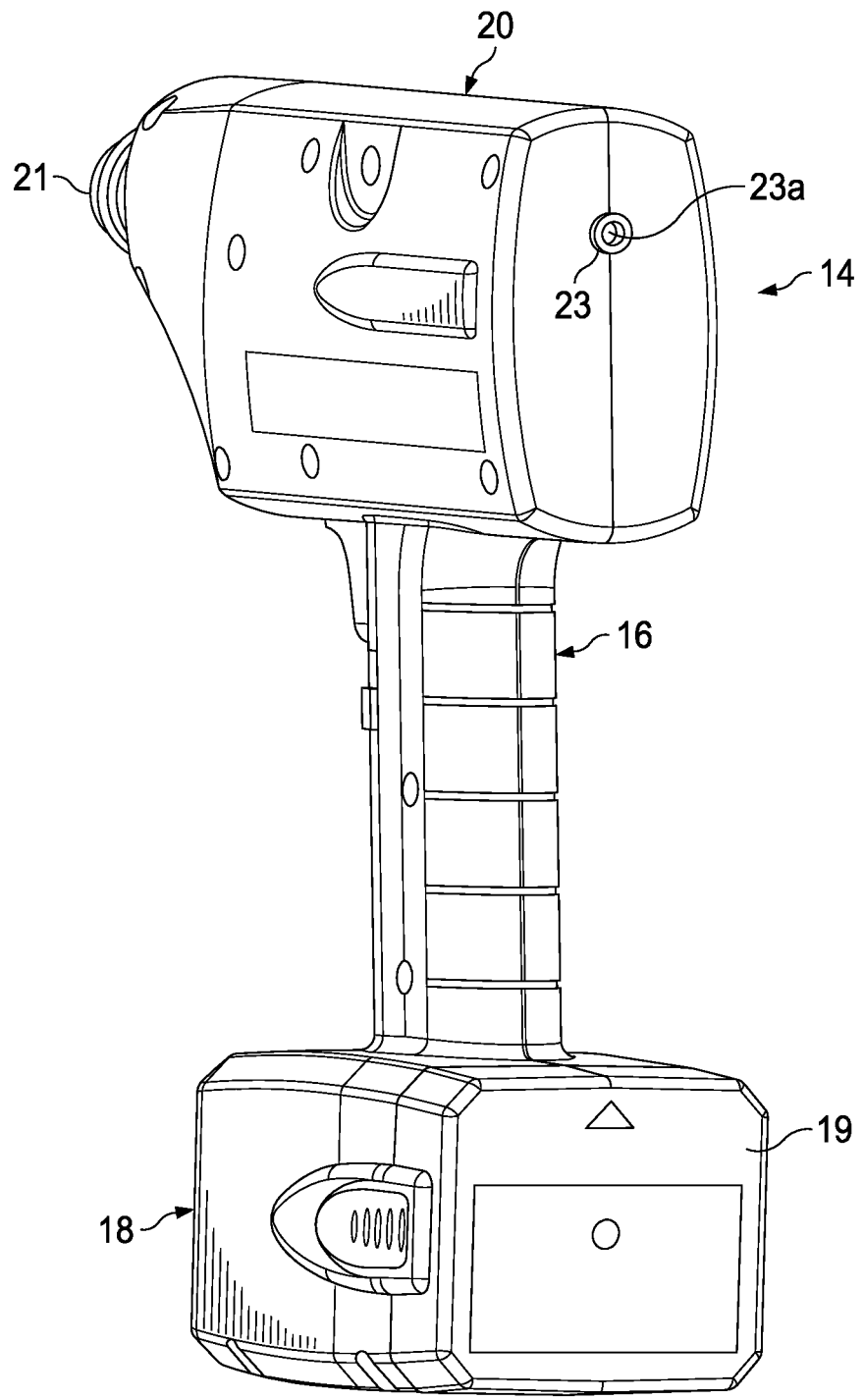
FIG. 11 is a perspective view illustrating the tool of FIG. 10 having the sealable door installed.

In FIG. 10, tool housing 14, including tool attachment portion 20, handle portion 16 and power source portion 18 are illustrated from a backside perspective. The power source portion 18, as stated above may be closed by the sealable door 19, shown removed. A cavity 25 in power source portion 18 may receive a battery on-site when the sterilized tool is being made ready for use. When sterilized, cavity 25 is exposed due to door 19 being removed and thus, the interior or cavity 25 of the power source portion 18 is also sterile. In FIG. 11, door 19 is illustrated in attachment with power source portion 18, thereby sealingly closing cavity 25. Also, a rear cannulation opening 23, FIGS. 10 and 11, not required for saw blade attachment tools, is shown on a backside wall or surface of tool attachment portion 20 opposite a front sidewall where chuck 21 is located. In this manner, a guide wire or pin can be fed through the tool attachment portion 20 via the cannulation opening 23 and exit via the chuck end for use with a cannulated attachment. A seal 23a, is provided to seal opening 23. The seal 23a may be either a removable seal or a penetratable seal.

Figure 12:
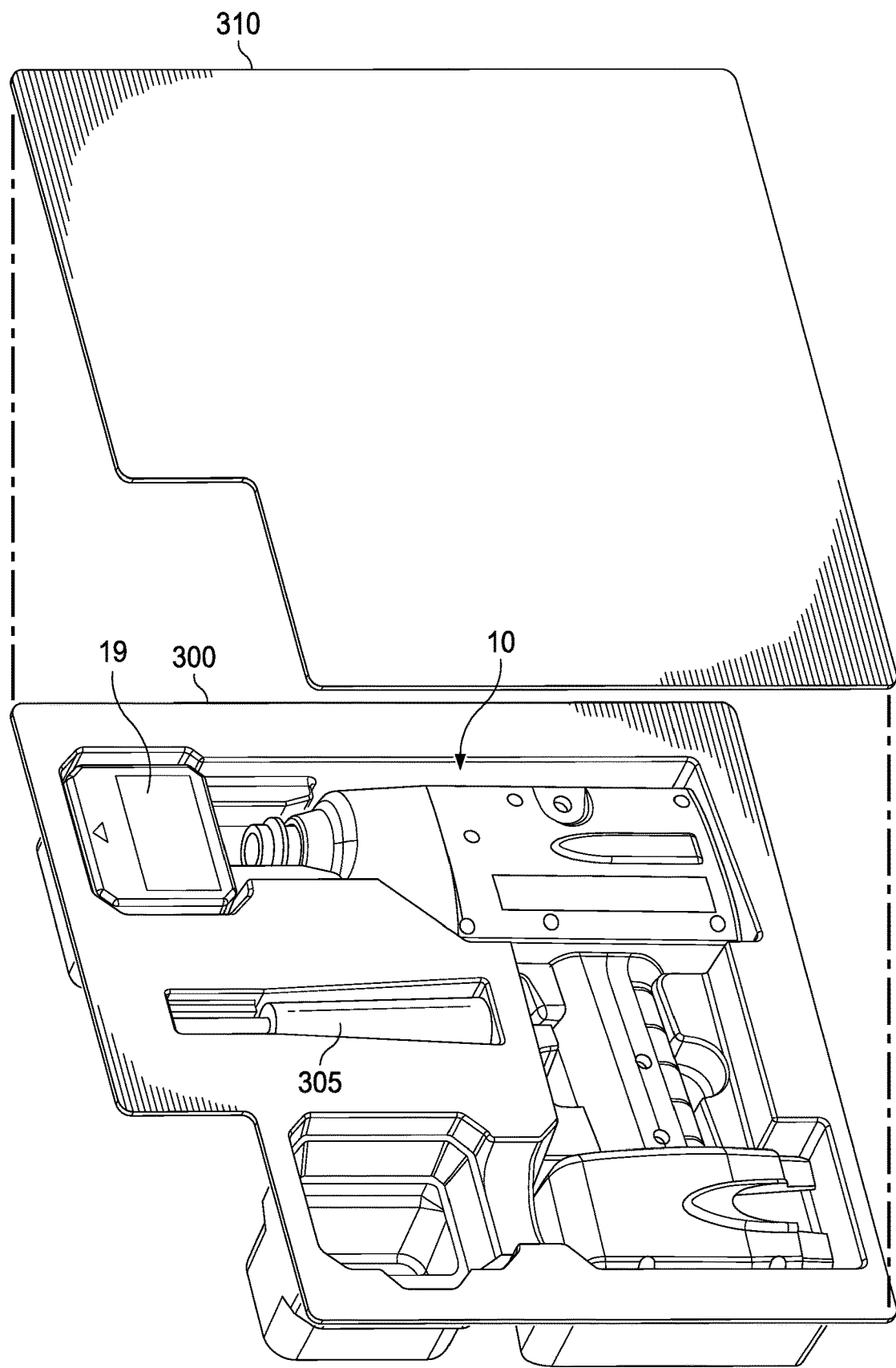
FIG. 12 is a perspective view illustrating an embodiment of a sterilized shipping tray and lid containing the power tool.

The limited use tool 10, FIG. 12, is returned to a re-supplier or re-processor to be prepared for re-use by packaging and sterilizing the tool. The single-use, contamination-blocking cover 12 is removed. During repackaging, the tool 10 is placed in a partitioned tray 300 for shipping. Also, the removable, sealing access door 19 is placed in the tray 300 to be used after a battery is placed in a cavity within the power source portion 18 on-site. The tray 300, containing the tool 10, access door 19 and a handle 305 available for two-handed operation (optional), are trayed and covered with a Tyvek lid or cover 310. Then a known ETO sterilization process, or other suitable process, sterilizes the contents of tray 300 in a gas chamber. Typically, a substantial number of the trayed tools are sterilized together for efficiency. Repackaged, sterilized trays 300 containing the tool 10 and access door 19 are then shipped to the user. When used, a battery, stored at the user's surgical facility is placed into the sterile cavity 25 in the power portion 18. The sterile door 19 is then installed in the access opening of cavity 25 (discussed above, see also FIG. 10).

The present disclosure has recognized and addressed many of the foregoing limitations and drawbacks of others concerning the need to provide hospitals and surgery centers with an improved, more reliable system of cost-effective, battery-operated, motorized tools in conjunction with better cleaning and maintenance protocols. In practice, the disclosed tooling system utilizes a concept called limited-use tools (LUT) and specifically, a new cover or enclosure system to make reprocessing of the LUT more efficient. This cover or enclosure would be used only once in the operating room, then would be removed and discarded at the reprocessing facility. A new, single-use enclosure would be installed at the reprocessing facility prior to final testing, packaging and re-sterilization of the LUT. The term "limited-use" as applied to orthopedic surgical tools can mean having a limited useful life, or a restricted lifespan for intended use. Preferably in this context, limited-use is intended to mean the number of surgeries where the useful life of the tool ranges from more than one use to less than 50 surgeries, and more preferably where the useful life of the tool ranges from more than one use to less than 30 surgeries, and most preferably where the useful life of the tool ranges from more than one use to less than 20 surgeries.

In a broad respect this disclosure teaches a method of improving (i.e. reducing) potential risk factors associated with infection control, and reduction of potential disease and infection transmission due to lapses in cleaning and infection control associated with routine maintenance of reusable powered surgical instruments. In another broad respect, the disclosure teaches a method of processing battery-operated tools used in surgery, to improve the cleanliness of instruments used in multiple surgical procedures and reduce the potential for disease and infection transmission due to lapses in cleaning and infection control procedures between procedures. In yet another broad respect, the disclosure teaches a method of logistical process of powered tools to improve cleanliness, operational efficiencies and performance. Still further it is to be understood that although this disclosure discusses the invention in terms of battery operated tools, one skilled in the art would fully appreciate that this disclosure has similar application to any pneumatic, wired or electric wall socket-powered instruments as well.

Although illustrative embodiments have been shown and described, a wide range of modification, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A reusable medical procedure power tool comprising:
   an enclosed rigid body mechanical housing including a tool attachment portion having a chuck or blade adapter for releasably receiving and holding an attachment portion for receiving and holding an attachment tool such as a drill bit or saw blade, a handle portion comprising an actuating trigger, and a forward-reverse switch and a power source portion for a battery pack:
   at least a two-piece contamination-blocking and closely conforming material outer shell cover mounted over the rigid body mechanical housing, the cover being a single use, removable and disposable contamination blocking cover, configured for removal and replacement after each medical procedure;
   the housing having a first shape and the at least a two-piece cover having a second shape substantially matching and substantially covering the first shape such that the cover includes a tool attachment portion, a handle portion and a power source portion; and
   the handle portion of the cover including a flexible tactile feel portion being movable sufficient to move an associated trigger attached to the handle portion,
   wherein the cover is removed and replaced after each medical procedure, prior to re-sterilization of the re-assembled power tool.

2. The tool of Claim 1, wherein the disposable contamination blocking over comprises a hard-shell member covering the housing with flexible inserted areas for controls actuation, wherein the selection of hard-shell materials and alloys/laminates comprises:
   PETG & A/PET;
   Polystyrene;
   Acrylic;
   Polycarbonate;
   ABS;
   Nylon;
   Polyolefin;
   Polyetheretherketone PEEK;
   Polyetherimide PEI;
   Polyetersulfone PES;
   Polyvinylidene PVDF;
   Polymethylpentene PMP;
   Polysulfone PSO;
   Ethylene-chlorotrifluoroethylene ECTFE; or
   metals.

3. The tool of Claim 1, wherein the disposable contamination blocking cover comprises a soft/flexible shell membrane covering the housing that covers and protects the majority of the tool 10 from contamination by blood/bone/tissue during a procedure, wherein the selection of flexible materials comprises:

Synthetic Paper;
C-Flex;
Flexible PVC;
Polycarbonate;
Polyester;
Polyethylene;
Polypropylene;
Nylon; or
Polyolefin.

4. The tool of claim 1, wherein the disposable contamination blocking cover comprises a soft/flexible stretch shell member covering the housing, wherein the selection of flexible materials comprises:

a. Silicone; b. Latex Rubber; c. Synthetic Rubber; d. Polychloroprene; or e. Flexible PVC.

5. The tool of claim 1, wherein the housing comprises materials and alloy laminates comprising:

a. PETG & A/PET;
b. Polystyrene;
c. Acrylic;
d. Polycarbonate;
e. ABS;
f. Nylon;
g. Polyolefin;
h. Polyetheretherketone PEEK;
i. Polyetherimide PEI;
j. Polyetersulfone PES;
k. Polyvinylidene PVDF;
l. Polymethylpentene PMP;
m. Polysulfone PSO;
n. Ethylene-chlorotrifluoroethylene ECTFE; or
o. metals.

6. The tool of claim 1 wherein the disposable outer shell cover comprises a flexible material, wherein the selection of flexible materials comprises:

a. Synthetic Paper b. C-Flex c. Flexible PVC d. Polycarbonate e. Polyester f. Polyethylene g. Polypropylene h. Nylon i. Polyolefin.

* * * * *

UNITED STATES PATENT AND TRADEMARK OFFICE
CERTIFICATE OF CORRECTION

| | |
|---|---|
| PATENT NO. | : 10,952,804 B1 |
| APPLICATION NO. | : 15/965887 |
| DATED | : March 23, 2021 |
| INVENTOR(S) | : Peter M Aman et al. |

It is certified that error appears in the above-identified patent and that said Letters Patent is hereby corrected as shown below:

On the Title Page

Item (73) should be:
(73) Assignee: Insurgical, Inc., Austin, TX (US)

Signed and Sealed this
Third Day of September, 2024

*Katherine Kelly Vidal*

Katherine Kelly Vidal
*Director of the United States Patent and Trademark Office*